(12) United States Patent
Luneau et al.

(10) Patent No.: US 11,041,271 B2
(45) Date of Patent: Jun. 22, 2021

(54) DEPOSIT DETECTION IN A PAPER MAKING SYSTEM VIA VIBRATION ANALYSIS

(71) Applicant: Ecolab USA Inc., St. Paul, MN (US)

(72) Inventors: Dominic Luneau, Victoriaville (CA); Fouad M. Moukannas, Lorraine (CA); Gary S. Furman, St. Charles, IL (US); David I. Weinstein, Hawthorn Woods, IL (US); William Von Drasek, Oak Forest, IL (US)

(73) Assignee: Ecolab USA Inc., Saint Paul, MN (US)

( * ) Notice: Subject to any disclaimer, the term of this patent is extended or adjusted under 35 U.S.C. 154(b) by 209 days.

(21) Appl. No.: 16/169,513

(22) Filed: Oct. 24, 2018

(65) Prior Publication Data
US 2019/0120811 A1  Apr. 25, 2019

Related U.S. Application Data

(60) Provisional application No. 62/576,416, filed on Oct. 24, 2017.

(51) Int. Cl.
*D21F 1/32* (2006.01)
*D21G 9/00* (2006.01)
(Continued)

(52) U.S. Cl.
CPC .............. *D21F 1/32* (2013.01); *D21G 3/005* (2013.01); *D21G 3/04* (2013.01); *D21G 9/0027* (2013.01)

(58) Field of Classification Search
CPC . D21F 1/32; D21G 3/00; D21G 3/005; D21G 3/02; D21G 3/04; D21G 9/00;
(Continued)

(56) References Cited

U.S. PATENT DOCUMENTS 1,924,154 A † 8/1933 Engert
3,061,944 A  11/1962 Kraus et al.
(Continued)

FOREIGN PATENT DOCUMENTS

CN  202401341 U  8/2012
CN  103194927 B  5/2015
(Continued)

OTHER PUBLICATIONS

WO 2012/055897, English language machine translation [epo.org]. (Year: 2012).*
(Continued)

*Primary Examiner* — Eric Hug
(74) *Attorney, Agent, or Firm* — Fredrikson & Byron, P.A.

(57) ABSTRACT

Vibration sensors can be used in paper making systems and methods to determine various aspects of the paper making operation. Vibration sensors, for example, positioned on cleaning blades configured to clean various deposits off of rollers in a paper making system can output vibration data that can be indicative of the vibration of the blade. The vibration data can be analyzed in order to characterize the cause of the vibration and/or the location of the vibration within a paper making system. If the vibration data satisfies a predetermined condition, a corrective action can be initiated. Different corrective actions can be initiated based on the characterized cause and/or location of the vibration in order to effectively improve the operation of the system while minimizing costly system shut downs and major maintenance.

24 Claims, 7 Drawing Sheets

(51) Int. Cl.
  *D21G 3/00* (2006.01)
  *D21G 3/04* (2006.01)

(58) Field of Classification Search
  CPC .. D21G 9/0009; D21G 9/0027; D21G 9/0036; D21G 9/0045; D21G 9/0054
  USPC .................. 162/198, 199, 272, 280–282
  See application file for complete search history.

(56) References Cited

U.S. PATENT DOCUMENTS

| | | | |
|---|---|---|---|
| 4,320,582 | A | 3/1982 | Klippstein et al. |
| 4,924,420 | A | 5/1990 | Hadley et al. |
| 5,123,152 | A | 6/1992 | Tenkula et al. |
| 5,179,150 | A | 1/1993 | Furman, Jr. et al. |
| 5,187,219 | A | 2/1993 | Furman, Jr. |
| 5,278,620 | A | 1/1994 | Godlove |
| 5,571,382 | A | 11/1996 | Berglund |
| 5,879,279 | A | 3/1999 | Berger et al. |
| 6,139,686 | A | 10/2000 | Trokhan et al. |
| 6,203,962 | B1 | 3/2001 | Itami et al. |
| 6,260,004 | B1 | 7/2001 | Hays et al. |
| 6,275,781 | B1 | 8/2001 | Maness et al. |
| 6,463,775 | B1 | 10/2002 | Kodama et al. |
| 6,579,418 | B2 * | 6/2003 | Lindsay .............. D21F 1/48 162/198 |
| 6,615,709 | B1 | 9/2003 | Suomi et al. |
| 6,928,370 | B2 | 8/2005 | Anuzis et al. |
| 7,027,953 | B2 | 4/2006 | Klein |
| 7,264,692 | B2 † | 9/2007 | Isometsa |
| 7,286,964 | B2 | 10/2007 | Kim |
| 7,691,236 | B2 | 4/2010 | Conn et al. |
| 7,850,823 | B2 | 12/2010 | Chou et al. |
| 7,962,086 | B2 | 6/2011 | Kato |
| 8,160,467 | B2 | 4/2012 | Zona et al. |
| 9,194,083 | B2 | 11/2015 | Echeverria et al. |
| 9,239,549 | B1 † | 1/2016 | Ishii |
| 9,404,895 | B2 † | 8/2016 | Von Drasek |
| 9,506,192 | B2 | 11/2016 | Johnson et al. |
| 9,518,359 | B2 | 12/2016 | Brauns et al. |
| 9,534,970 | B1 | 1/2017 | Figiel |
| 9,562,861 | B2 | 2/2017 | Von Drasek et al. |
| 9,873,981 | B2 * | 1/2018 | Edbauer .............. D21G 3/005 |
| 2004/0035540 | A1 | 2/2004 | Maeenpaeae et al. |
| 2005/0034831 | A1 | 2/2005 | Beuther et al. |
| 2005/0157327 | A1 | 7/2005 | Shoji et al. |
| 2006/0090574 | A1 | 5/2006 | Moore et al. |
| 2006/0182451 | A1 | 8/2006 | Shoji et al. |
| 2006/0281191 | A1 | 12/2006 | Duggirala et al. |
| 2007/0125891 | A1 | 6/2007 | Crossley et al. |
| 2007/0127934 | A1 | 6/2007 | Shoji et al. |
| 2007/0137820 | A1 | 6/2007 | Yasugahira et al. |
| 2008/0013818 | A1 | 1/2008 | Shakespeare |
| 2008/0023168 | A1 | 1/2008 | Conn et al. |
| 2008/0033695 | A1 | 2/2008 | Sahara et al. |
| 2009/0190939 | A1 | 7/2009 | Satoh et al. |
| 2010/0086672 | A1 | 4/2010 | Von Drasek et al. |
| 2010/0299119 | A1 | 11/2010 | Erikson et al. |
| 2012/0073775 | A1 | 3/2012 | Duggirala et al. |
| 2015/0075928 | A1 | 3/2015 | Johnson et al. |
| 2016/0340830 | A1 | 11/2016 | Von Drasek et al. |

FOREIGN PATENT DOCUMENTS

| | | | |
|---|---|---|---|
| DE | 102005052858 A1 | 5/2007 | |
| DE | 202009008818 U1 | 11/2009 | |
| DE | 102011085220 A1 | 5/2012 | |
| FI | 115145 B | 3/2005 | |
| GB | 1577664 A | 10/1980 | |
| JP | S5609493 A | 1/1981 | |
| JP | H11012977 A | 1/1999 | |
| JP | 3117936 B2 | 12/2000 | |
| JP | 2001523774 A | 11/2001 | |
| JP | 2010217512 A | 9/2010 | |
| WO | 2004005615 A1 | 1/2004 | |
| WO | 2004040983 A1 | 5/2004 | |
| WO | 2004113611 † | 12/2004 | |
| WO | 2011002377 A1 | 1/2011 | |
| WO | 2012055897 † | 5/2012 | |
| WO | 2012055897 A1 | 5/2012 | |
| WO | WO 2012/055897 * | 5/2012 | .............. D21G 1/00 |
| WO | 2013156147 A1 | 10/2013 | |

OTHER PUBLICATIONS

Vahasalo et al., "White pitch deposition and styrene-butadiene-rubber binder content in paper mill process waters," Appita Journal, vol. 59, No. 4, 2006, pp. 280-284.

Voltaire et al. "Acoustic emission and tack of heat-set inks during selling on MWCpapers and fountain solution emulsification," Nordic Pulp & Paper Research Journal, vol. 22, No. 4, 2007, pp. 432-440, Abstract Only.

Voltaire et al., "Acoustic characterisation of film splitting in a HSWO printing nip," Nordic Pulp & Paper Research Journal, vol. 22, No. 4, 2007, pp. 424-431, Abstract Only.

Voltaire et al., "Use of an on-press acoustic sensor to monitor coldset offset printing of newspaper," Nordic Pulp & Paper Research Journal, vol. 21, No. 3, 2006, pp. 323-327, Abstract Only.

Voltaire et al., "Acoustic investigation of cavitation noise from offset ink film splitting," Nordic Pulp & Paper Research Journal, vol. 21, No. 3, 2006, pp. 314-322, Abstract Only.

Kosuga et al., "Reduction of Pitch Deposit Troubles by Coagulant Derived from Waste Corrugated Board," Japan Tappi Journal, vol. 58, No. 4, 2004, pp. 468-477, Abstract Only.

Beck, "Stickies in recycle pulp for use in fine paper—the search for a precise method," TAPPI Press, Recycling Symposium, New Orleans, Mar. 3-6, 1996, pp. 271-277, Abstract Only.

Sithole et al., "A laboratory test to predict deposition in recycled paper making," TAPPI Press, Recycling Symposium, Chicago, Apr. 14-16, 1997, pp. 367-371, Abstract Only, (HCAPLUS).

Zwart et al., "The struggle for paper uniformity," TAPPI Press, International Engineering Conference, Miami, Sep. 13-17, 1998, vol. 1, pp. 243-251, Abstract Only.

Welkener et al., "The effect of furnish components on depositability of pitch and stickies," Nordic Pulp & Paper Research Journal, vol. 8, No. 1, 1993, pp. 223-225, Abstract Only.

Douek et al., "Some aspects of pitch control with talc in unbleached kraft pulps," Journal of Pulp and Paper Science, vol. 17, No. 5, 1991, pp. 171-177, Abstract Only.

Goryacheva et al., "Mechanical-chemical methods for the deresinification of pulp," Bumazhnaya Promyshlennost (1976), (3), 11, Abstract Only.

Shevchenko et al., "Combining stickies monitoring and control in recycling," TAPPI Press, 2010 Tappi Peers Conference and 9th Research Forum on Recycling (2010), vol. 1, pp. 809-854, Abstract Only.

Murcia, "Combining stickies monitoring and control in tissue manufacturing from recycled fiber," Tissue World Americas 2010—5th International Conference and Exhibition for the North and South American Tissue Business (2010), 9 p., Abstract Only.

Bomela et al., "Effect of stator chording and rotor skewing on performance of reluctance synchronous machine," IEEE Transactions on Industry Applications (Jan. 2002), vol. 38, No. 1, pp. 91-100, Abstract Only.

Bomela et al., "Effect of machine design on performance of reluctance synchronous machine," Conference Record of the 2000 IEEE Industry Applications Conference. Thirty-Fifth IAS Annual Meeting and World Conference on Industrial Applications of Electrical Energy, Rome, Italy, 2000, vol. 1, pp. 515-522, Abstract Only.

Bomela et al., "Effect of stator chording and rotor skewing on average torque and torque ripple of reluctance synchronous machine," 1999 IEEE Africon. 5th Africon Conference in Africa, Cape Town, South Africa, 1999, vol. 2, pp. 687-690, Abstract Only.

Hyvarinen et al., "Infrared analyzers for process measurements," Proceedings of SPIE—The International Society for Optical Engineering, vol. 1762, 1992, pp. 187-192, Abstract Only.

(56) References Cited

OTHER PUBLICATIONS

Padley, "Maximising performance through state-of-the-art chemistry solutions," Int. Papwirtsch., No. 4, 2009, pp. 19-22, Abstract Only.
Herbst, "Construction of paper: to survive processing," PTS Symposium 2008: paper and imaging, Munich, Germany, Oct. 15-16, 2008, 22 pages, Abstract Only.
Kerman, "Fixative selection and runnability optimization in different paper grades using the Ciba Contaminant Analyzer (CCA)," Progress 08. 16th International papermaking conference. Efficiency in papermaking and converting processes, Krakow, Poland, Sep. 23-26, 2008, 16 pages, Abstract Only.
Kermann et al., "Novel approach for the selection and optimisation of fixatives for pitch and sticky control in various fibre systems," 17th PTS CHT symposium: chemical technology of papermaking, Munich, Germany, Sep. 12-15, 2006, Paper 34, 21 pages, Abstract Only.
Holopainen et al., "Online machinery condition monitoring avoids unexpected failures and improves operator safety," Appita Journal, vol. 58, No. 1, Jan. 2005, pp. 18-21, Abstract Only.
Anon, (62nd) Pulp and Paper Research Conference, Tokyo, Japan, Jun. 1-2, 1995, Japan TAPPI, 1995, 156 pages, Abstract Only.
International Patent Application No. PCT/US2018/057319, International Search Report and Written Opinion dated Jan. 4, 2019, 13 pages.
Kuny, "New sensors for online property measurements," Wochenbl. Papierfabr., vol. 134, No. 23-24, Dec. 2006, pp. 1415-1418.
Sithole et al., "A laboratory test to predict deposition in recycled paper making," TAPPI Press, Recycling Symposium, Chicago, Apr. 14-16, 1997, pp. 367-371, Abstract Only, (PIRA).
Holopainen et al., "Online machinery condition monitoring avoids unexpected failures and improves operator safety," Appita Journal, vol. 58, No. 1, Jan. 2005, pp. 18-21, Abstract Only, (PIRA).
Agarwal, "Asynchronous Analog to Digital Converters: Architectures and Circuits," Dissertation, Tufts University, Aug. 2010, pp. 1-112.
Akazawa et al., "Study on Regenerative Chatter Vibration in Ball End Milling of Flexible Workpieces," IEEE, 2008, 6 pages.
Alessadrini et al.,"Chatter Marks: Origin, Evolution and Influence of the Creping Doctors," Ind. Carta, vol. 41, No. 4, Jun. 2003, pp. 120-129.
Arato, Jr. et al., "Automatic faults diagnosis by application of neural network system and condition-based monitoring using vibration signals," Proceedings of the 2008 IAJC-JJME International Conference, ISBM 978-1-0643-379-9.
Archer et al., "Chatter and Soft Tissue Production: Process Driven Mechanisms," Tissue World Americas, Feb.-Mar. 2009, pp. 33-35.
Claveau et al., "Mechanical Vibration Analysis Using an Optical Sensor," IEEE, 1996, pp. 876-879.
Fugate et al., "Vibration-based damage detection using statistical process control," Mechanical Systems and Signal Processing, vol. 15, Issue 4, Jul. 2001, pp. 707-721.
Heng et al., "Rotating machinery prognostics: State of the art, challenges and opportunities," Mechanical Systems and Signal Processing, vol. 23, 2009, pp. 724-739.
Jagannathan, "Test and theory for robust active vibration control of rotor-bearing systems utilizing piezoelectric actuators," Dissertation, Texas A&M University, 1993, 213 pages.
Jeong et al., "A Fault Diagnosis on Rotating Machinery Using the Mahalanobis Taguchi System," Mechanical Engineering Department, Hanyang University, Korea, Jul. 2009, 7 pages.
Messaoud et al., "Detection of chatter vibration in a drilling process using multivariate control charts," Computational Statistics & Data Analysis, vol. 52, 2008, pp. 3208-3219.
Rehorn et al., "State-of-the-art methods and results in tool condition monitoring: review," International Journal of Advanced Manufacturing Technologies, vol. 26, 2005, pp. 693-710.
Sohn et al., "Damage diagnosis using time series analysis of vibration signals," Smart Materials and Structures, vol. 10, 2001, pp. 446-451.
Wicklin, What is Mahalanobis distance, SAS Institute Inc, Feb. 15, 2012.
Zhang et al., "Statistical condition monitoring based on vibration signals," Proceedings VETOMAC-3 & ACISM-2004, pp. 1238-1243, New Delhi, India.

\* cited by examiner
† cited by third party

DEPOSIT DETECTION IN A PAPER MAKING SYSTEM VIA VIBRATION ANALYSIS

RELATED MATTERS

This application claims priority to U.S. Provisional Patent Application No. 62/576,416, filed Oct. 24, 2017, the entire contents of which are incorporated herein by reference.

BACKGROUND

During paper manufacturing processes, a paper sheet is formed from paper stock in a paper making system, for example, on a carrier traveling between a series of rollers, and can be dried on one or more heated drying cylinders, for example, for tissue sheets, on a single large drying cylinder, termed a Yankee or Yankee dryer. During the paper making process, deposits from the paper stock can form on various rollers or other locations in the system, which can lead to inefficient operation unless the system is cleaned.

Systems can include cleaning blades positioned in the system that are intended to remove some such deposits, for example, from rollers in the system. However, blades can wear out and/or become coated by such deposits, reducing the effectiveness of the blades for cleaning the system. Blade cleaning or replacement can be costly from the standpoint of requiring the system to be shut down for service, since downtime reduces the paper output of the system.

Additionally, deposits forming in the system that can negatively impact paper quality are often realized by detecting defects in the paper produced from the system, which is not necessarily a reliable indicator of deposits forming in the system. Additionally, even if such visual inspection does lead to the detection of excessive deposits, paper that has already been produced by the system is of a lower quality than desired, which can lead to loss of the product and the time spent producing the defective product. Further time and resources are required to address the problem, for example, by shutting down and cleaning the system. This leads to additional losses in output of the system, which can be costly for the paper product manufacturer.

SUMMARY

Aspects of the disclosure are generally directed toward systems and methods for monitoring the vibration of cleaning blades positioned in a paper making system. Exemplary paper making systems can include a plurality of guide rollers including a first guide roller and a carrier forming a continuous surface contacting the plurality of guide rollers. A paper stock source can be configured to provide a paper stock to a paper side of the carrier.

Such systems can include a cleaning blade associated with and arranged to clean the first guide roller. In some examples, systems can include a vibration sensor coupled to the cleaning blade configured to detect vibration of the cleaning blade. A controller can receive vibration data from the vibration sensor representative of the vibration of the cleaning blade and analyze the received vibration data. In some embodiments, if the vibration data satisfies a predetermined condition, the controller can be configured to initiate a corrective action.

In some cases, vibration of the cleaning blade can be indicative of excessive deposits forming on the first guide roller, causing the vibration. Such deposits at the first guide roller can be indicative of overall increased deposits forming throughout the system, which can lead to various problems during paper making processes. Thus, in some examples, the controller can analyze the vibration data to determine a possible cause of a determined predetermined condition, such as the presence of excess vibration and/or deposition within the system. In various systems, one or more cleaning blades associated with one or more rollers can include associated vibration sensors for sensing vibration at various locations within the system. Vibration data from such one or more positions can be used to characterize the causes of vibration, such as type of deposits forming, amount of deposits forming, and the like. Corrective actions can be determined from such characterization.

In some such systems, the controller can initiate a corrective action specific to the determined cause of vibration and/or deposits in order to reduce the number and/or rate of deposits in the system, improving and/or prolonging operation of the system. For example, systems can include a first chemical source in communication with the controller, such as one or more of water, fixitives, dispersants, surfactants, coagulants, solvents, release agents, and detackifiers. In some such examples, initiating the corrective action can include changing an amount of chemical dispensed from the first chemical source, for example, at one or more particular locations in the system to reduce deposit formation.

DETAILED DESCRIPTION

Aspects of the disclosure are generally related to systems and methods for detecting deposits forming in any of a variety of locations during a paper making process. Further aspects of the disclosure are generally related to systems and methods for reducing the amount of the detected deposits and/or preventing the future buildup of additional deposits.

Figure 1:
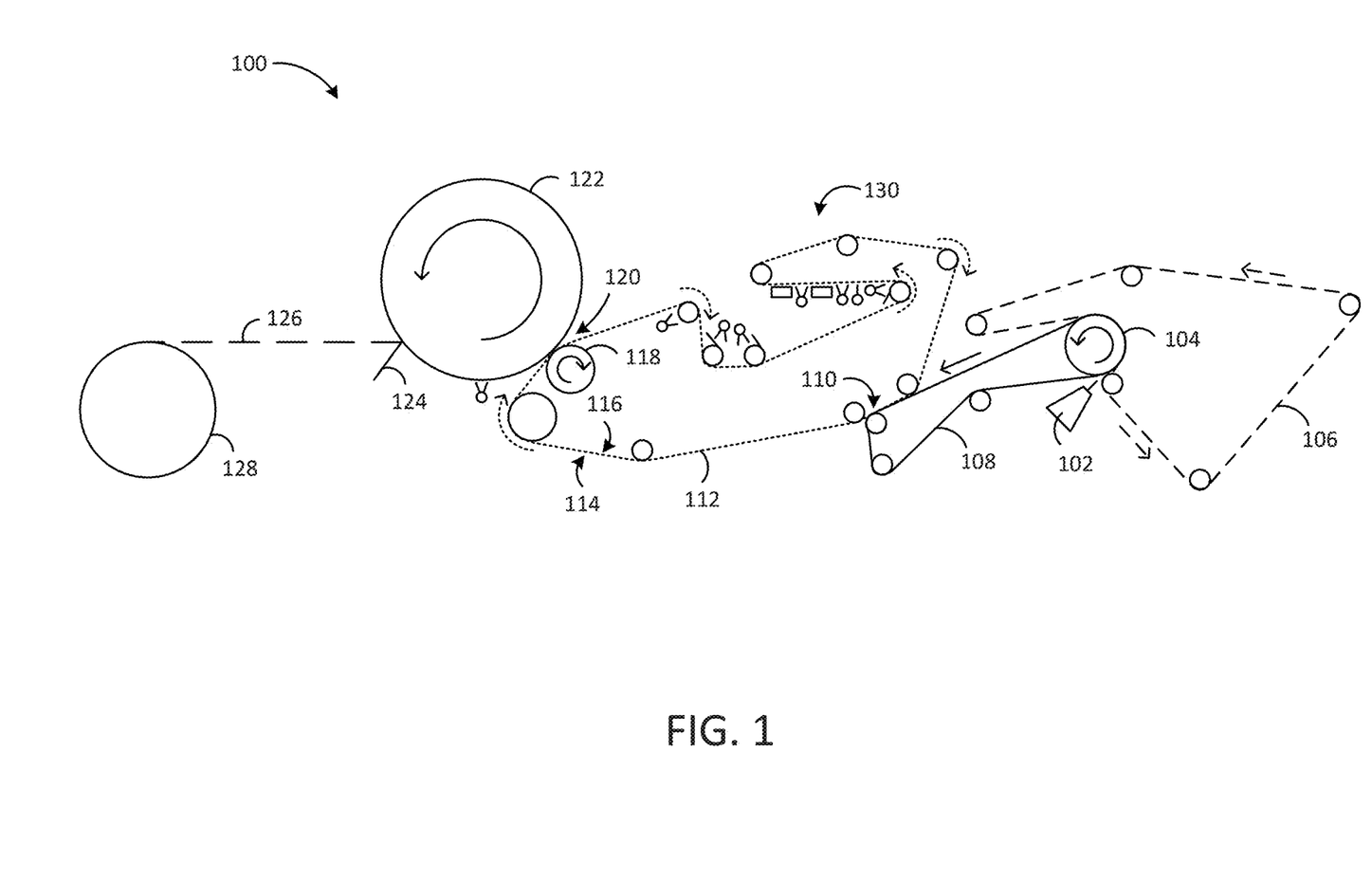
FIG. 1 shows a high-level schematic diagram of an exemplary paper making system.

FIG. 1 shows a high-level schematic diagram of an exemplary paper making system. The system of FIG. 1 is exemplary and shows only one particular example of a paper making system, for example, a tissue machine. Those skilled in the art will appreciate that many examples and configurations of paper making machines are possible and that aspects of the invention described herein will be applicable to any appropriate systems, not just those illustrated by way of the exemplary figures. For example, additional paper machine types can include machines configured to produce any of a variety of grades of paper, including but not limited to: tissue, towel, napkins, nonwovens, paperboard, packaging, linerboard, corrugated medium, printing and writing papers, newsprint, market pulp, and specialty grades.

The system 100 of FIG. 1 includes a headbox 102 that is configured to provide paper stock into the system 100 to be processed. In the illustrated examples, the stock from the headbox 102 is received at a forming roller 104 as part of a twin-wire system (having wires 106 and 108). The stock travels along wire 108 to a nip 110 between the wire 108 and a carrier 112. In some examples, the carrier 112 comprises a felt material. Exemplary felt materials can include a woven material made from polyamide yarn, for example, arranged in a different layered designs. Other exemplary carrier 112 materials can include, but are not limited to, forming fabrics, belts (e.g. NTT belts such as provided by Valmet Corporation of Espoo, Finland), transfer fabrics and belts, and through-air fabrics.

As shown, the carrier 112 has a paper side 114 onto which the stock is received from the wire 108 at the nip 110 and a back side 116 opposite the paper side. The carrier 112 travels around a series of rollers with the back side 116 of the carrier contacting the rollers until the carrier 112 encounters a press roller 118. At the press roller 118, moisture is pressed from the stock and the stock is transferred to a dryer 122 (e.g., a Yankee dryer) at nip 120. In the illustrated example, the stock dries at the dryer 122 and is creped via a creping blade 124 to form a sheet 126 which is received by a roller 128 for storage or further processing.

After the paper product is transferred from the carrier 112 to the dryer 122 at nip 120, the carrier continues through a series of rollers in a carrier conditioning section 130, before returning to the nip 110 to receive the paper stock from the wire 108. Rollers can interface with both the paper side 114 and the back side 116 of the carrier 112 as the carrier traverses around the rollers in the carrier conditioning section 130. Such rollers can be used to guide the carrier 112 through the paper making system 100 to prepare the carrier 112 for receiving paper stock material at nip 110 for continuing the paper making process. As will be described elsewhere herein, in some examples, the carrier conditioning section 130 further includes additional components, such as chemical sources, sprayers, dryers, vacuums, and the like to facilitate the conditioning of carrier 112 for further use.

As shown in FIG. 1, the carrier moves generally in a clockwise direction around the rollers. However, there are sections, for example, in the carrier conditioning section 130, in which the carrier 112 does not always travel in the clockwise direction. Thus, unless otherwise specified, when referred to herein as traveling in a given direction (e.g., a first direction), a system component (e.g., the carrier 112) is generally traveling in that system direction rather than an absolute direction. For example, in the illustrated example of FIG. 1, the carrier 112 travels around a series of rollers in a first direction, despite at times traveling clockwise or counter-clockwise around various rollers.

Figure 2:
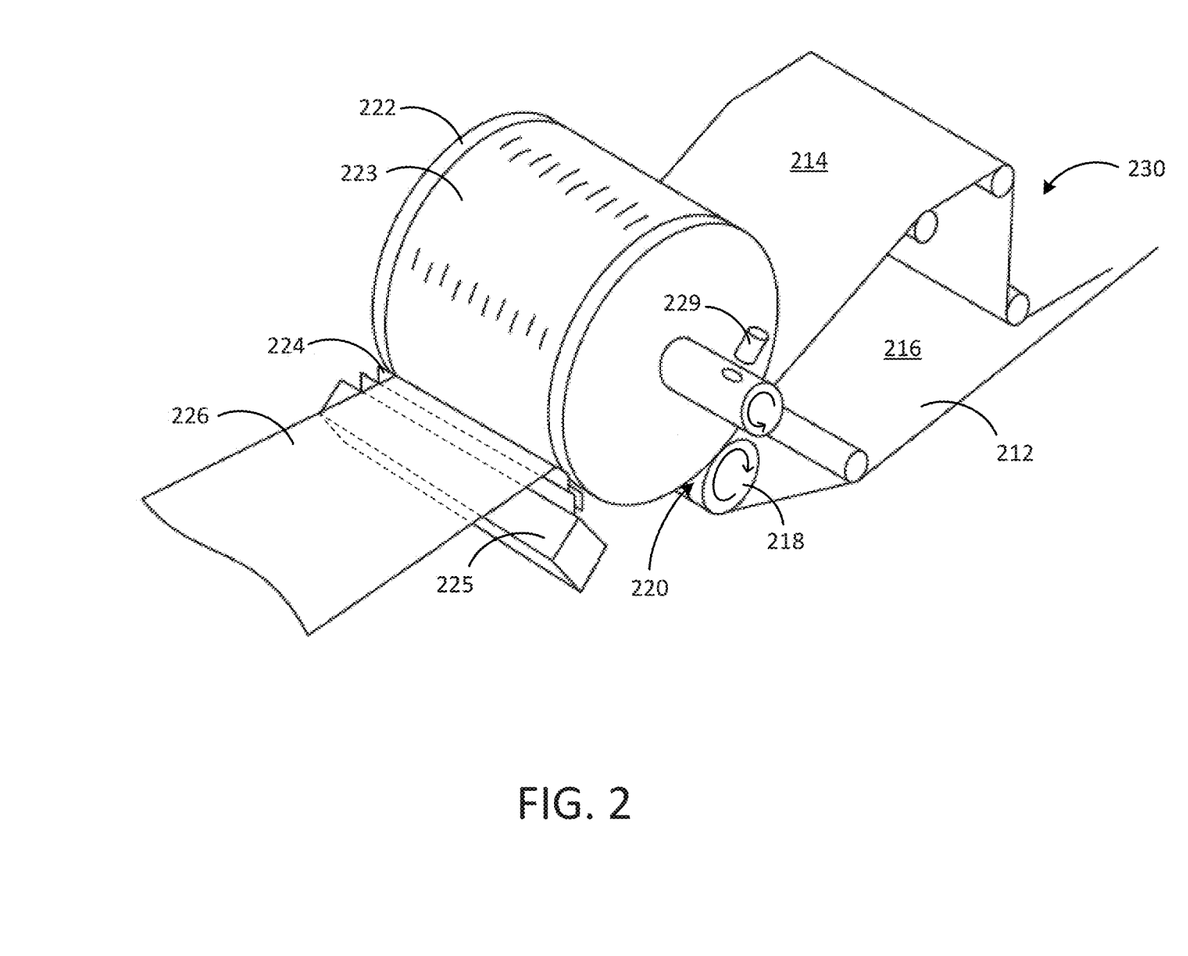
FIG. 2 is a perspective view of a portion of a paper making system.

FIG. 2 is a perspective view of a portion of a paper making system. The illustrated section in FIG. 2 includes a carrier 212 having a paper side 214 and a back side 216 extending around a plurality of rollers. A nip 220 between press roller 218 and a dryer 222 causes paper stock from the paper side 214 of the carrier 212 to be transferred from the carrier 212 to the dryer 222. A blade holder 225 positioned proximate dryer 222 includes a creping blade 224 for creping dried paper product 223 from the dryer 222 to form a creped sheet 226. In the example of FIG. 2, the dryer 222 includes a tachometer 229 that can be used to measure the number of rotations of the dryer 222. It will be appreciated that, while tachometer 229 is positioned on the rotational axis of dryer 222, one or more such tachometers can be positioned anywhere throughout the paper making system. Additionally, as many of the system components rotate in concert with one another (e.g., dryer 222 and press roller 218), and if the dimensions of various components are known, rotation speeds and/or linear speeds of different system components may be calculated using a single tachometer (e.g., 229) measurement. After transferring the paper stock onto the dryer 222 at nip 220, the carrier 212 travels through a carrier conditioning section 230 where the carrier 212 can be processed and prepared to receive more paper stock.

Figure 3:
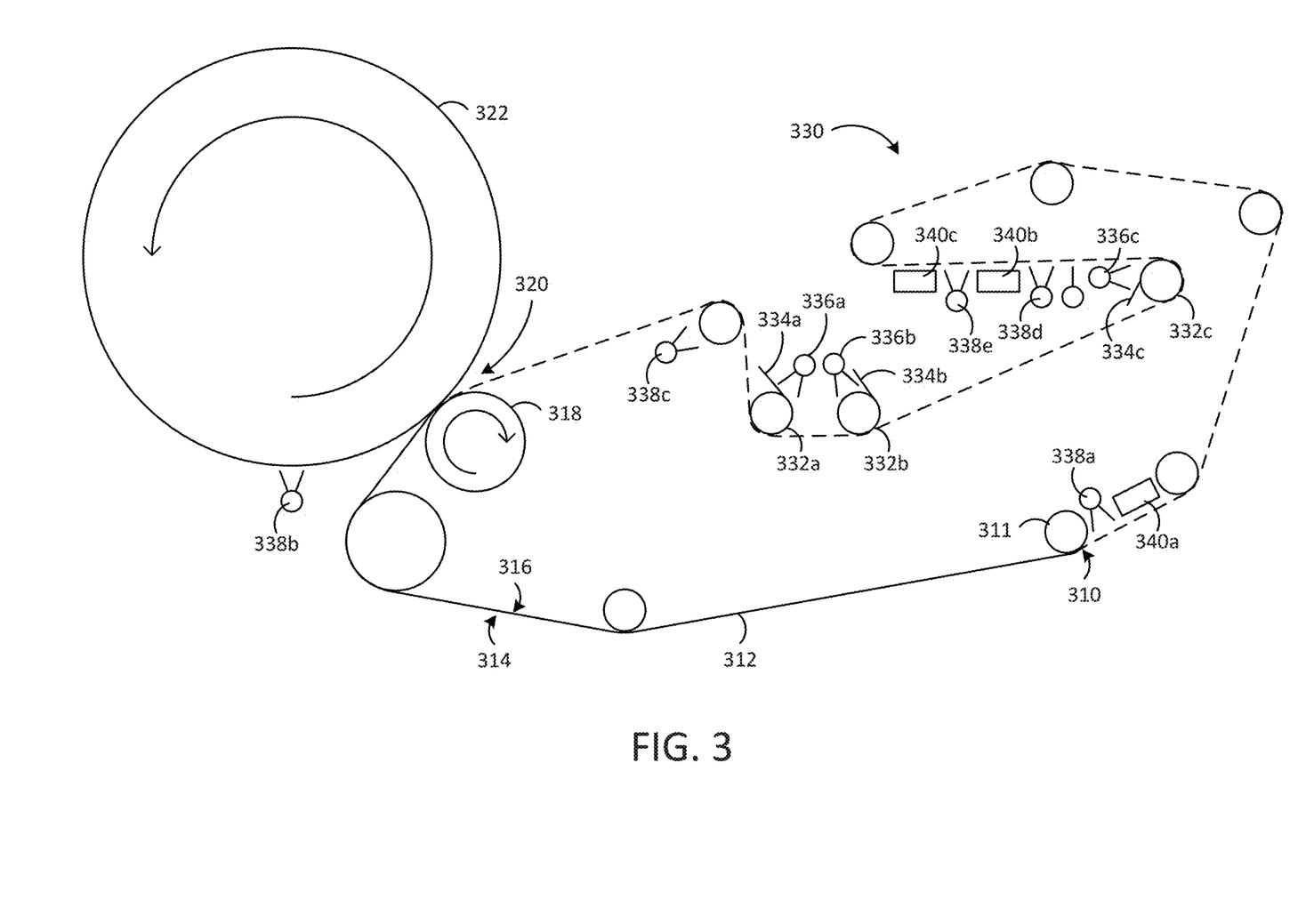
FIG. 3 is a schematic diagram showing a part of a papermaking system.

FIG. 3 is a schematic diagram showing a part of a papermaking system. The illustrated portion of system 300 includes a carrier 312 having a paper side 314 and a back side 316. The carrier 312 contacts and travels around a plurality of rollers in the system 300. As described, for example, with respect to FIG. 1, the carrier can receive paper stock to be carried by the carrier 312 to other components in the system 300. In the illustrated example, the carrier 312 receives paper stock at a nip 310 proximate roller 311 onto the paper side 314 of the carrier. The paper stock is carried by the carrier to a nip 320 including press roller 318 and dryer 322, where the paper stock is transferred from the carrier 312 to the dryer 322.

After transferring the paper stock at nip 320, the carrier 312 continues through a carrier conditioning section 330 of the system until it returns to nip 310 to receive more paper stock. In the illustrated example, the portion of the carrier 312 in the carrier conditioning section 330 of the system 300 is shown in a broken line. In this section, the carrier 312 often includes little or no paper stock, as it has been transferred to the dryer 322 at nip 320. By contrast, the carrier 312 is shown in a solid line between nip 310 and nip 320, when the carrier 312 is carrying paper stock on its paper side 314.

In the exemplary schematic of FIG. 3, the carrier conditioning section 330 includes a plurality of rollers that interface with one of the paper side 314 and the back side 316 of the carrier 312. The carrier conditioning section 330 includes rollers 332a, 332b, and 332c that interface with the paper side 314 of the carrier 312 after the paper stock has been substantially transferred to the dryer 322. In some examples, rollers 332a, 332b, and 332c can collect debris that remains on the paper side 314 of the carrier 312 after transferring the paper stock onto the dryer 322. For example, deposits known as "stickies" can adhere to the carrier 312 after the paper stock is transferred to another section in the paper making system (e.g., the dryer 322). The carrier 312 can be guided through the carrier conditioning section 330 via a plurality of rollers (e.g., 332a-c) such that the paper side 314 and/or the back side 316 of the carrier 312 are subjected as desired to one or more cleaning processes (e.g., at chemical sources 338d, 338e and vacuums/blowers 340b, 340c described elsewhere herein) to remove the stickies from the carrier 312.

In some examples, while guiding a fouled carrier 312 through the carrier conditioning section 330 of system 300, rollers (e.g., 332a-c) can undesirably collect deposits (e.g., stickies) from the carrier 312, resulting in an undesirable buildup of deposits on such rollers. In the example of FIG. 3, rollers 332a, 332b, 332c each have a cleaning blade 334a, 334b, 334c, respectively, associated therewith. Each cleaning blade 334a, 334b, 334c can be used to scrape against the surface of its respective roller 332a, 332b, 332c as the roller rotates in order to clean deposits off its surface. For instance, in an exemplary operation, roller 332a contacts the paper side 314 of the carrier 312. Deposits left on the carrier 312 after paper stock is transferred onto the dryer 322 can accumulate on the roller 332a as it contacts the carrier 312. As the roller 332a rotates, a surface of the roller 332a scrapes against the blade 334a, removing deposits from the surface of roller 332a. Further deposits may be transferred from the carrier 312 onto additional rollers 332b, 332c.

The exemplary system further includes chemical sources 336a, 336b, and 336c associated with rollers 332a, 332b, and 332c, respectively. Chemical sources 336a, 336b, and 336c can include, for example, spray bars that extend substantially in the longitudinal direction of corresponding rollers 332a, 332b, and 332c, respectively. In other examples, chemical sources 336a, 336b, and 336c can include single sprayers that spray toward corresponding rollers or at a lower angle relative to the longitudinal direction of the corresponding rollers. Chemical sources 336a, 336b, 336c can be arranged to introduce one or more chemicals into the system proximate respective rollers 332a, 332b, 332c. Such chemicals can be used to facilitate the cleaning and/or rinsing of the carrier 312 and/or roller associated with the particular chemical source. In some such examples, chemicals are applied to rollers (e.g., 332a-c) such that the chemicals are subsequently transferred to carrier 312 to facilitate the cleaning of the carrier 312.

Exemplary chemicals that can be used include water, dispersants, surfactants, coagulants, solvents, detackifiers, fixatives, release agents, and the like. In some examples, such chemicals can be introduced to the carrier 312 and/or to one or more rollers (e.g., 332a, 332b, 332c) continuously or periodically according to a processing schedule. In some examples, different chemical programs can be implemented to introduce one or more such chemicals upon initiation of such programs, for example, manually or automatically (e.g., per a schedule).

While the exemplary carrier conditioning section 330 of FIG. 3 includes three rollers (332a, 332b, 332c) contacting the paper side 314 of the carrier 312, each roller having an associated blade (334a, 334b, 334c) and chemical source (336a, 336b, 336c), it will be appreciated that a variety of alternative configurations are possible. For example, any number of rollers may be used. Rollers may be equipped with zero, one, two, or more blades for cleaning the surface thereof. Similarly, rollers may have zero, one, two, or more associated chemical sources configured to apply a chemical proximate the roller. In some instances, multiple rollers can share one or more blades and/or chemical sources. The carrier conditioning section 330 of FIG. 3 further includes a plurality of additional components, such as vacuums/blowers 340a, 340b, 340c and additional chemical sources 338a, 338b, 338c, 338d, and 338e positioned throughout the system. Such components can be used to clean the carrier 312 and/or assist in transferring paper product to or from the carrier 312.

The system shown in FIG. 3 further includes additional components that can be used to facilitate the cleaning and/or preparation of the carrier 312 to receive more paper stock to continue the paper making process. Additional chemical sources 338a, 338b, 338c, 338d, 338e are positioned throughout the system to provide chemicals to the carrier 312 and/or various rollers throughout the system. Some such rollers contact the back side 316 of the carrier 312. Other components, such as vacuums/blowers 340a, 340b, 340c are similarly placed throughout the system for facilitating cleaning and/or preparation of the carrier 312 and/or transfer of the paper product.

Figure 4:
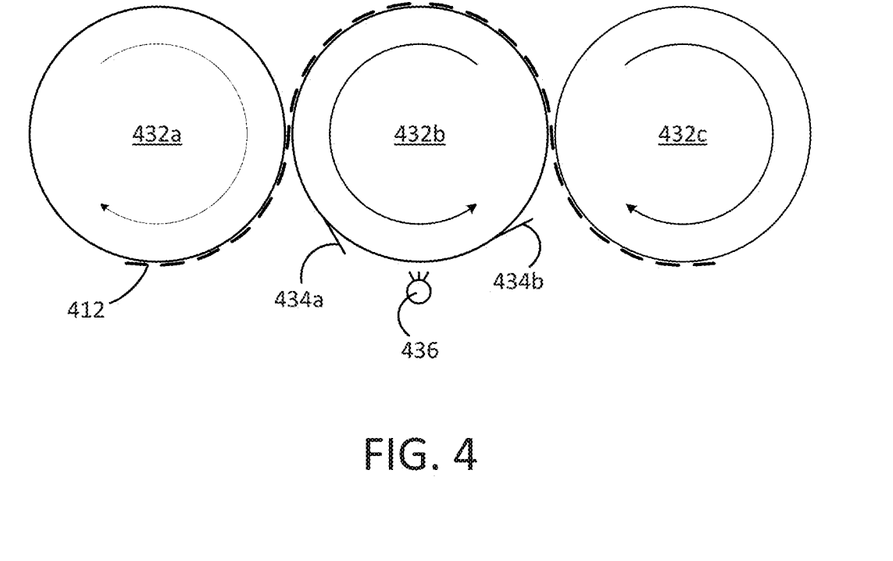
FIG. 4 shows a schematic illustration of an alternative roller configuration.

As described, FIGS. 1 and 3 show exemplary configurations of rollers through and around which one or more carriers travels during a paper making process. FIG. 4 shows a schematic illustration of an alternative roller configuration. In the example of FIG. 4 a sheet 412 travels through a plurality of rollers 432a, 432b, 432c. In various embodiments, rollers 432a, 432b, 432c can include press rollers, drying rollers, a center roller configuration, or the like. Such an exemplary arrangement of rollers can be found in various locations throughout a paper making system. In some embodiments, sheet 412 includes a carrier with a paper product disposed on one side of the carrier. In other examples, sheet 412 comprises a pair of carriers (e.g., two felt materials) with the paper product disposed between the two carriers such that the paper stock does not engage any of rollers 432a, 432b, or 432c. In still further examples, the sheet 412 includes paper product directly contacting rollers 432a, 432b, and 432c.

In some examples, deposits (e.g., stickies) form on rollers 432a, 432b, 432c, for instance, from the paper side of a carrier or from a paper product interfacing with roller directly. In the example of FIG. 4, blades 434a, 434b are positioned such that, as roller 432b rotates, the surface of roller 432b scrapes against blades 434a, 434b, for example, to clean the surface of the roller 432b. A chemical source 436 is positioned proximate roller 432b for providing a chemical to roller 432b and/or blades 434a, 434b. In some examples, one or more chemicals provided via chemical source 436 can be used, for example, to assist in removing deposits formed on the roller 432b. Additionally or alternatively, chemicals can be used in a sheet release application to assist in transferring the sheet 412 (e.g., a paper material directly contacting the rollers) between rollers. In some such examples, chemicals provided by chemical source 436 can include oils and oil-surfactant blends. It will be appreciated that the exemplary configuration of FIG. 4 is another possible example of how blades and a chemical source can be positioned proximate one or more rollers in a paper making system, though other configurations are possible.

Figure 5:
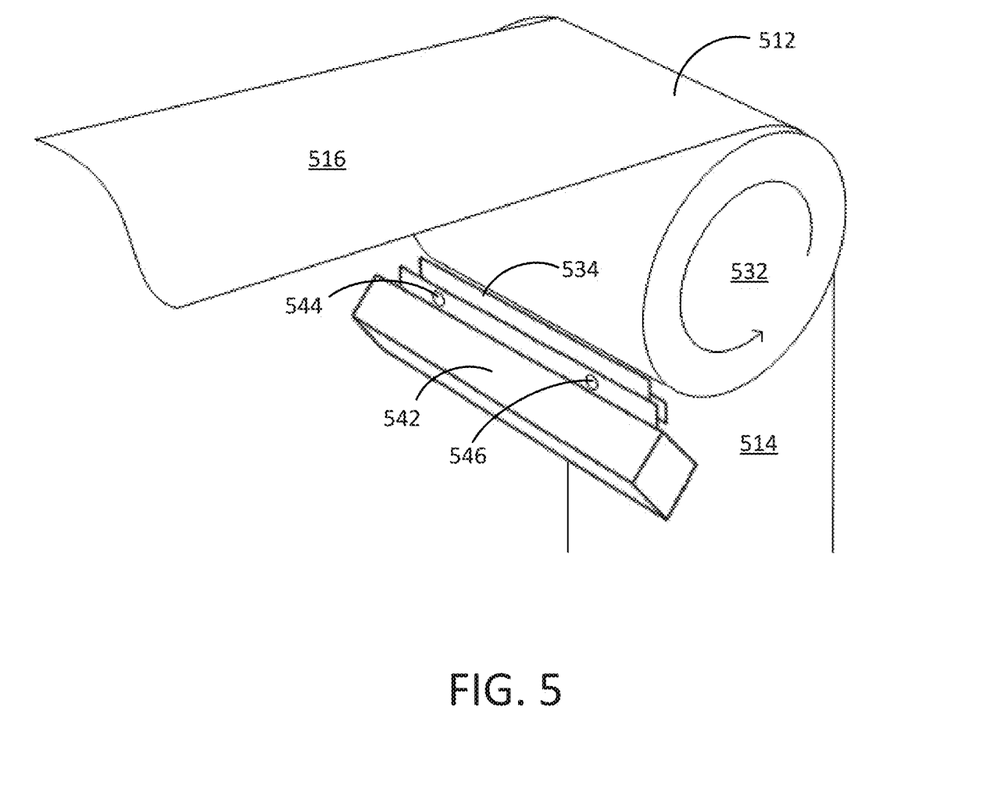
FIG. 5 shows a perspective view of a roller and a cleaning blade proximate the roller for cleaning a surface thereof.

FIG. 5 shows a perspective view of a roller and a cleaning blade proximate the roller for cleaning a surface thereof. As shown, roller 532 engages the paper side 514 of a carrier 512. As described elsewhere, in other examples and/or other locations in the system (e.g., the carrier conditioning section 330 of FIG. 3), a roller can instead engage the back side 516 of the carrier 512.

From the perspective of FIG. 5, the roller 532 rotates counter-clockwise as the carrier 512 moves through the system. The system includes a blade 534 supported by a blade holder 542 such that the roller 532 surface scrapes against the blade 534 as the roller 532 rotates. In some examples, the blade 534 and/or the blade holder 542 can be positionable so that the blade 534 selectively engages or disengages from the roller 532, for example, via manual and/or automated movement of the blade 534 and/or blade holder 542. As described elsewhere herein, the blade 534 can be used to scrape and clean the surface of the roller 532, for example, to remove deposits such as stickies from the roller 532.

In some examples, a blade (e.g., 534) can be associated with one or more vibration sensors configured to detect vibration of the blade and generate vibration data representative thereof. In the illustrated example, vibration sensors 544 and 546 are positioned on blade holder 542 to detect vibration of the blade 534 and/or blade holder 542 during a cleaning process. In some examples, the blade 534 and the blade holder 542 are rigidly attached to one another so that vibration of the blade 534 and the blade holder 542 are substantially the same. Additionally or alternatively, vibration sensors (e.g., 544, 546) can be positioned directly on the blade 534 for measuring the vibration thereof. Exemplary vibration sensors can include accelerometers, such as piezoelectric accelerometers, micro electro-mechanical systems (MEMS), piezoelectric films, non-contact optical vibration sensors (e.g., fiber optic vibration monitoring), or other appropriate accelerometers.

The illustrated example of FIG. 5 includes vibration sensors 544 and 546 positioned toward opposite ends of blade holder 542. In some such examples, the vibration of each end of the blade 534 and/or blade holder 542 can be analyzed individually. While two vibration sensors (544 and 546) are shown in the embodiment of FIG. 5, it will be appreciated that a variety of configurations are possible. For instance, in some embodiments, a single vibration sensor can be positioned on the blade holder 542 or on the blade 534 itself, such as in the center of the blade 534 or blade holder 542. In other examples, three or more vibration sensors can be positioned on a blade (e.g., 534) or blade holder (e.g., 542) for detecting vibration of the blade during operation. The vibration experienced by the blade 534 and/or the blade holder 542 during operation can be useful for determining a condition of one or more system components.

Figure 6:
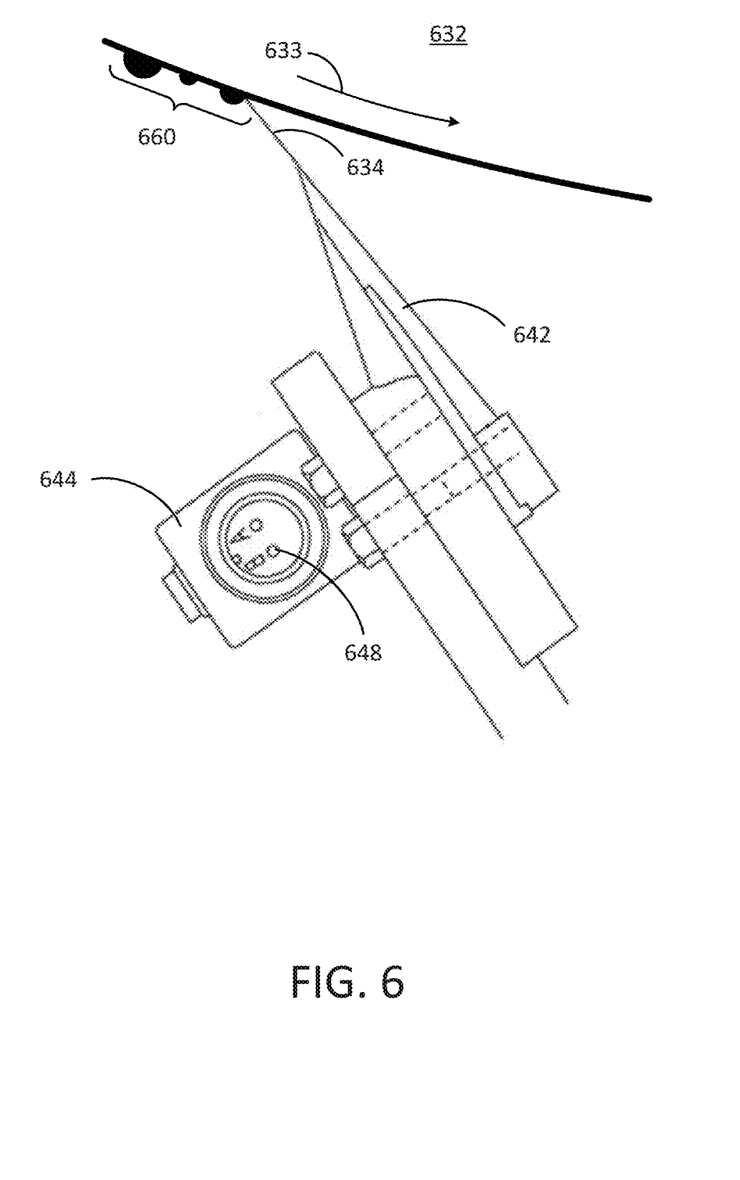
FIG. 6 is a cross-sectional view of a blade cleaning a roller.

FIG. 6 is a cross-sectional view of a blade cleaning a roller. In the example of FIG. 6, blade holder 642 supports a blade 634 against a surface of a roller 632. The roller 632 is shown as rotating in the direction of arrow 633 so that the surface of roller 632 scrapes against the blade 634. During operation, as the roller 632 rotates, deposits 660 (e.g., stickies) on the surface of the roller 632 encounter blade 634, and are removed from the surface. Thus, the blade 634 can be used to clean the surface of the roller 632.

The blade holder 642 includes a vibration sensor 644 attached thereto configured to detect vibration of the blade 634 and/or the blade holder 642. The vibration sensor 644 includes an interface 648 for interfacing with one or more external components. In various examples, interface 648 can provide power to the vibration sensor 644. Additionally or alternatively, the interface 648 can be used to communicate data to or from the vibration sensor 644 to another component, such as a system controller. In some embodiments, the interface 648 is capable of wired and/or wireless communication.

In some instances, the vibration experienced by the blade 634 is a function of various properties of deposits 660 on the roller 632 surface. For example, the size, number, hardness, or other properties of deposits 660 can contribute to the vibration of the blade 634 during operation of the system, for example during a cleaning process. Accordingly, vibration data generated by the vibration sensor 644 and received from the interface 648 can be analyzed for determining information regarding deposits 660 on the roller 632.

In various paper making systems or processes, one or more such cleaning blades can be used as shown in FIG. 6 to clean the surface of one or more rollers. For example, referring back to FIG. 3, cleaning blades 334a, 334b, and 334c can be arranged similar to cleaning blade 634 in FIG. 6 relative to rollers 332a, 332b, and 332c, respectively. Additionally or alternatively, one or more vibration sensors (e.g., 544, 546 in FIG. 5) can be associated with each blade for which the vibration is detected. The vibration data from one or more vibration sensors positioned on one or more rollers can be analyzed to determine, for example, details regarding deposits (e.g., 660) on the respective rollers.

In some embodiments, data gathered from the one or more vibration sensors can be used to detect unfavorable deposit buildup on the corresponding rollers. For instance, in some examples, the greater amount of stickies being deposited on rollers implies a greater concentration of stickies in the paper stock in the paper making process, which can lead to issues in the paper quality. For example, excess stickies in the paper stock can lead to problems in the appearance of the paper product, defects or holes in the finished product, and the like. Additionally or alternatively, deposits accumulating on the carrier 312 and/or the rollers can cause the paper quality to suffer. For instance, with reference to FIG. 3, if the carrier 312 is dirty (e.g., with a buildup of stickies), a dirty carrier might negatively impact the dewatering process that occurs at the press roller 318 to assist in drying the paper stock. Additionally, deposits that remain on the felt could lead to holes in the paper product transferred from the carrier, which can lead to a paper product with defects and/or undesired breaking of the paper sheet during future processing. Accordingly, the vibration data from one or more vibration sensors can be used to treat or prevent the buildup of excess deposits in the system.

Figure 7:
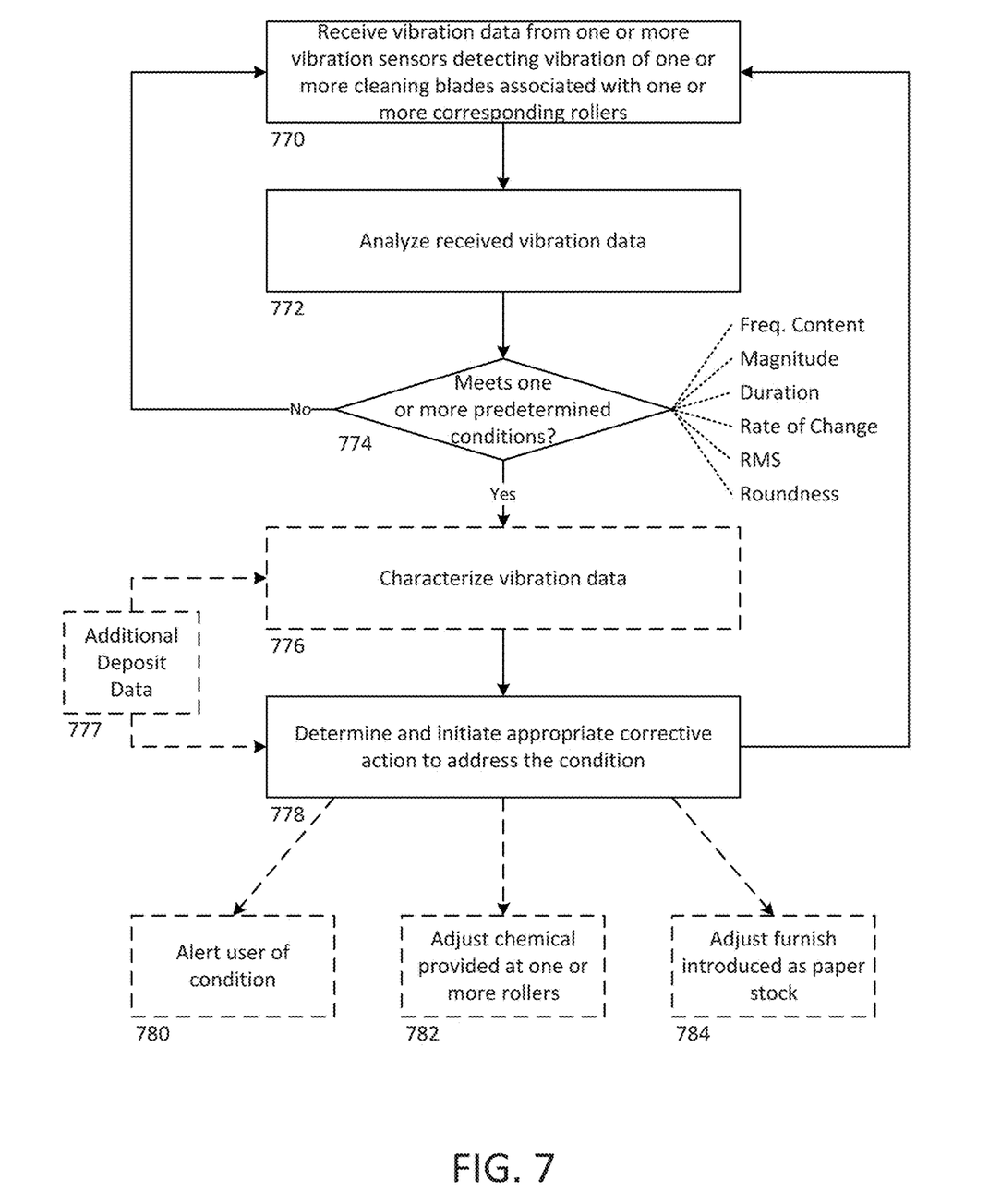
FIG. 7 is a process flow diagram illustrating an exemplary method for addressing the detection of excess deposits in a paper making system.

FIG. 7 is a process flow diagram illustrating an exemplary method for addressing the detection of excess deposits in a paper making system. The method includes the step of receiving vibration data from one or more vibration sensors detecting vibrations of one or more cleaning blades associated with one or more corresponding rollers (770). The received vibration data can be analyzed (772) to determine if the vibration data meets one or more predetermined conditions (774). As shown in FIG. 7, exemplary parameters that can be associated with such one or more predetermined conditions can include, but is not limited to, the frequency content, magnitude, duration, rate of change (e.g., temporal derivative) of the vibration data or the RMS of the vibration data, the roundness profile of the vibration waveform data (e.g., changes and/or spikes in the average roundness profile), or combinations thereof. In general, one or more such parameters of the vibration data meeting a predetermined condition can include, for example, being above a predetermined threshold, below a predetermined threshold, or within a predetermined range of values. For instance, in some examples, determining if the vibration data meets one or more predetermined conditions comprises comparing the detected vibration magnitude to a threshold and determining of the magnitude exceeds the threshold. In other examples, meeting a predetermined condition can correspond to a magnitude of the vibration exceeding a threshold for a predetermined length of time in order to reduce the occurrences of false positives.

In some embodiments, analyzing the received vibration data (772) comprises analyzing the frequency content of the received vibration data, for example, via a Fast Fourier Transform (FFT) of the vibration data. In such embodiments, various frequency bands can be analyzed individually during vibration data analysis. For example, in some embodiments, the magnitude of the vibration in each of a plurality of frequency bands can be individually compared to a threshold for determining whether or not the vibration data meets one or more predetermined conditions (776). In some examples, the magnitude of each frequency band is compared to the same threshold, though in other examples, the magnitudes of different frequency bands can be compared to different thresholds. In still further examples, each frequency band can be compared to a threshold, and, the one or more predetermined conditions include one or more of a plurality of frequency bands exceeding its respective threshold for a predetermined amount of time.

In some examples, comparing the magnitude of detected vibration to a threshold (e.g., in the time domain or frequency domain) comprises comparing the magnitude to a plurality of thresholds indicating various degrees of vibration. In some such examples, each threshold is associated with a predetermined amount of time for which the threshold must be exceeded for vibration to be detected.

According to the method of FIG. 7, if the vibration data does not meet one or more predetermined conditions at step 774, then the process repeats, and vibration data is received (770) for further analysis. In some examples, new vibration data is received continuously. In other examples, vibration data is analyzed according to certain intervals, such as once per minute, once per hour, once per day, or the like. Additionally or alternatively, vibration analysis can be manually initiated, for example, by a system operator.

If the vibration data does satisfy one or more predetermined conditions at step 774, then an appropriate corrective action to address the detected condition is determined and initiated (778). In some examples, the appropriate corrective action simply comprises alerting a user of the detected condition (780). Once alerted, the user may, for example, inspect the system to determine the cause of the condition (e.g., excessive vibration). Inspecting the system can include investigating the system for a cause of vibration and/or excess deposits, shutting down the system for cleaning or other maintenance, or the like.

In some embodiments, if such a condition is detected at step 774, the vibration data is characterized (776). Characterizing the vibration data can be performed in a variety of ways, such as analyzing the frequency content of the vibration data. In some examples, the frequency content of the vibration data can represent various conditions of the roller associated with the blade for which the vibration data is being analyzed. For example, in some cases, the frequency content of the vibration data can differ depending on the types of deposits on the rollers (e.g., hard deposits, such as inorganic fillers, and soft deposits, such as adhesives).

In other examples, vibration data from a plurality of sensors can be analyzed together to characterize the vibration data. For instance, with reference to the exemplary system of FIG. 3, vibration sensors associated with blades 334a and 334c can independently produce vibration data representative of the vibrations at each blade individually. Predetermined condition(s) (e.g., vibration having a magnitude above a threshold) present at one blade compared to another can provide indications about the nature of deposits in the system. In another example, with reference to the illustrative example of FIG. 5, analyzing vibration data from both vibration sensor 544 and vibration sensor 546 can provide information about the location of possible deposits in the system on a given roller (e.g., 532).

Characterization of the vibration data such as the examples described above can provide additional information that can be useful for determining one or more appropriate corrective actions to address the detected one or more predetermined conditions, such as detected excess vibration. For instance, in an exemplary embodiment described with reference to FIG. 3, frequency analysis of vibration data for a cleaning blade 334a arranged to clean a corresponding roller 332a can provide information regarding the type of the deposits forming on the roller 332a and therefore present in the system. As described elsewhere herein, various chemicals can be used for assisting in the removal and/or prevention of such deposits from forming within the system (e.g., on the carrier 312 or other machine surfaces). For example, chemical source 336a can be used to provide a chemical to roller 332a to assist in the removal of the deposits forming proximate the roller 332a. Similarly, one or more predetermined conditions, such as excess vibration, at the blade 334a could indicate that a chemical usually applied to roller 332a (e.g., via chemical source 336a) or elsewhere in the system (e.g., via chemical source 338e) during a paper making process has been depleted and should be replenished. Accordingly, a corrective action to address detected vibration can include adjusting a chemical provided at one or more locations in the system (782).

In another example, with reference to FIG. 1, vibration data associated with a cleaning blade could be indicative of an improper furnish composition added as a paper stock material at headbox 102. Characterization of the vibration data may be used to identify an improper furnish, which may be corrected. Accordingly, another exemplary corrective action to address detected vibration can include adjusting a furnish introduced to the paper making system as paper stock (784). Exemplary ways of adjusting the furnish can include reducing a recycle content of the furnish or changing the type of recycle fiber (e.g., a cleaner type of fiber), such as using a fiber with a lower content of stickies and tackies and/or pitch.

In some embodiments, characterizing the vibration data (776) and/or determining and initiating a corrective action (778) can include analysis based on additional deposit data (777). For instance, data from other system components, such as an optical stickies monitor, a press effluent monitor, or a wet end monitor can provide additional information that can be useful in characterizing deposits in the system and/or determining appropriate corrective actions. One or more examples of such monitors are described in U.S. Pat. No. 9,562,861. In an exemplary embodiment, data from an optical stickies monitor can supplement detected vibration data to confirm the presence of stickies at one or more system locations. A press effluent monitor can provide an indication of how well a system component (e.g., a carrier, a roller, etc.) is being cleaned by, for example, a chemical source. In an exemplary process, detected excess vibration and minimal deposits present in the effluent stream can indicate that a currently employed process is not effectively removing deposits from a certain portion of the system. However, in some such cases, a noticed increase in deposits in the effluent stream can be an indication that a corrective action is effective in eliminating deposits from the system.

Additionally or alternatively, a wet end monitor can be used to monitor various parameters within the system, such as pH, conductivity, and turbidity of one or more chemical, furnish, or effluent streams. In some instances, parameters such as pH and conductivity provide information regarding the potential for deposit in the system. Turbidity values can indicate a relative cleanliness of the furnish being used. Such data can be useful in characterizing a source of deposits forming in the system and/or possible corrective actions to reduce the amount of deposits.

Various examples have been described. In some embodiments, various steps in the method of FIG. 7 can be performed manually by a user, automatically via, for example, a controller, or a combination thereof. In various systems, controllers can include any component or combination of components capable of receiving input data (e.g., vibration data from one or more vibration sensors), analyzing the received data, and providing an output based on the analyzed data. The output can include an alert (e.g., an indicator light, sounding an alarm, sending a message such as a text message, email, or other communication, etc.), a control signal to cause one or more other components to perform an action, or the like. In various examples, controllers can be embodied as one or more processors operating according to instructions included in a memory, such as a non-transitory computer-readable medium. Such memory can be integral with the controller or separate. In other examples, such a controller can be embodied as circuitry arranged to perform the prescribed tasks, such as an application-specific integrated circuit (ASIC).

In some embodiments, such a controller can be in communication with one or more vibration sensors and configured to receive (770) and analyze (772) the vibration data to determine if the vibration data meets one or more predetermined conditions (774), for example, excessive vibration in one or more frequency bands. The controller can be further configured to characterize the vibration data (776), such as performing frequency analysis of the vibration data. In some such examples, the controllers can, after characterizing the vibration data, determine and initiate appropriate corrective actions to address the detected one or more conditions (778).

In some embodiments, the controller can differentiate between different causes of predetermined conditions based on characterization of the vibration data. For instance, in an exemplary configuration, the controller can analyze the frequency content of vibration data provided by one or more vibration sensors associated with a cleaning blade (e.g., 334*a*), determine a likely type of deposit forming on the roller (e.g., 334*a*) associated with the blade. The controller can determine an appropriate course of action for addressing the particular type of deposit and initiate that action, such as causing a chemical source (336*a*) to apply or increase the application of a chemical for removing and/or inhibiting such deposits at the roller (332*a*). Additionally or alternatively, the controller can alert a user of one or more detected conditions (780). In some such instances, the controller can recommend a course of action the user may take to address the vibration based on the characterized vibration data. Possible courses of actions recommended to a user can include shutting down the system, cleaning one or more portions of the system, changing or sharpening one or more blades within the system, changing the furnish, applying a chemical, checking for a structural malfunction (e.g., of the blade holder), changing the loading pressure, purging the system (e.g., adding fresh water and/or eliminating some or all of the white water flowing through the system), or the like.

The process of FIG. 7 can be performed for one or more blades associated with one or more rollers. In some examples, the exemplary method in FIG. 7 can be performed for a plurality of blades consecutively or simultaneously. Characterizing the vibration data (776) can include analyzing vibration data individually from a plurality of blades and determine and initiate an appropriate corrective action at one or more of the rollers associated with the blades. Such corrective actions can be system-wide, and/or can be applied to individual locations within the system.

Figure 8:
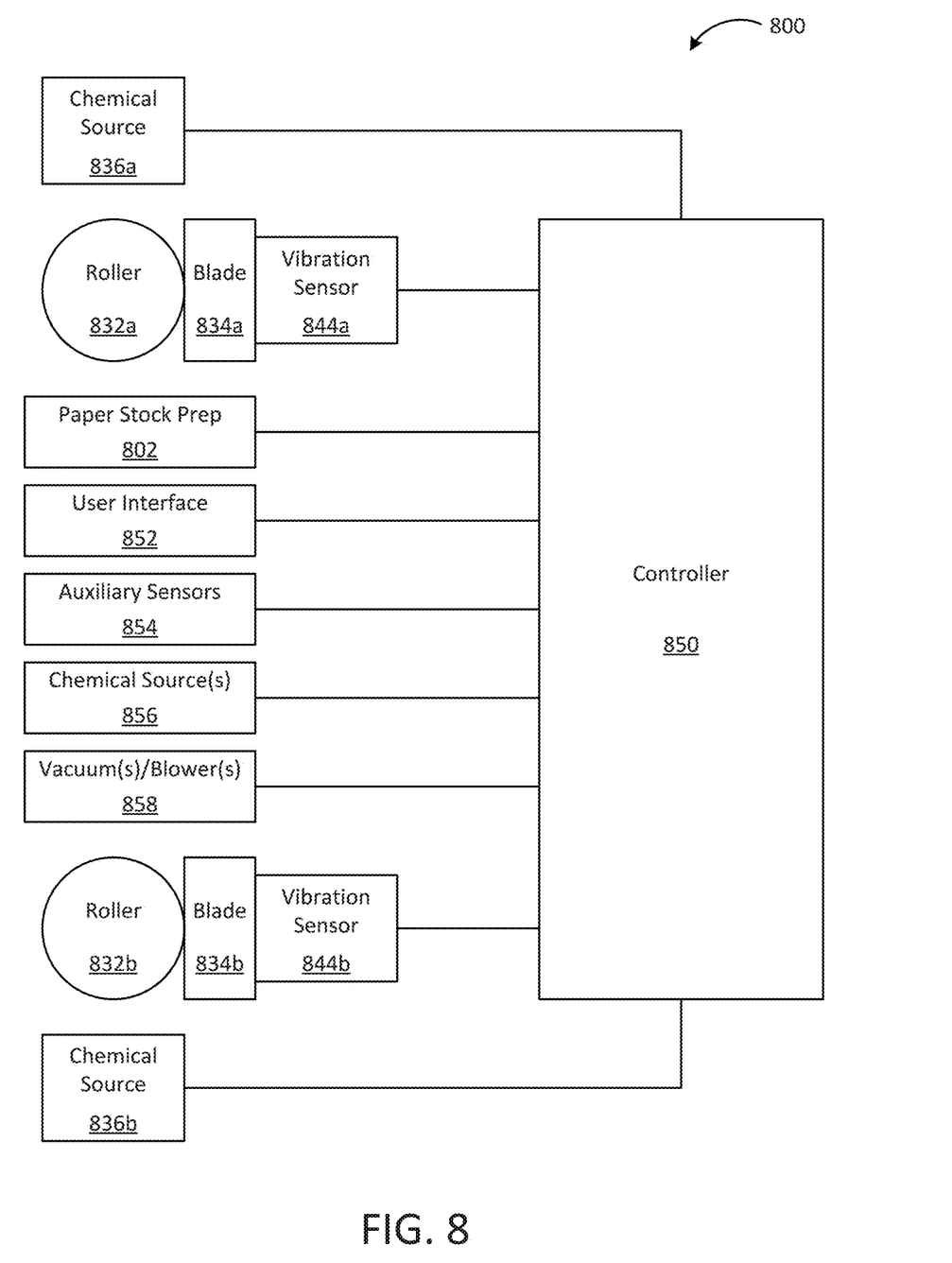
FIG. 8 is a schematic diagram illustrating communication between components in a paper making system.

FIG. 8 is a schematic diagram illustrating communication between components in a paper making system. In the illustrated embodiment, the system 800 includes a paper stock preparation location 802 which acts as a source of paper stock to the headbox and the paper making system. The system includes roller 832*a* and an associated blade 834*a* positioned proximate the roller 832*a*. In some examples, the roller 832*a* is on the wet end of a paper making process (e.g., upstream from a drying section wherein moisture is extracted from the paper stock, such as via a wet-press section and/or on a Yankee dryer). The roller 832*a* can be positioned in the paper making system such that it engages a carrier with or without paper stock present on the carrier. In some examples, the roller 832*a* comprises a guide roller. In other examples, roller 832*a* can include a press roller (e.g., 318 in FIG. 3), a motor-driven roller, guide roller, drying cans, or the like.

As described elsewhere herein, blade 834*a* can be positioned such that it scrapes against and cleans the surface of roller 832*a*. The blade 834*a* can include a vibration sensor 844*a* configured to generate vibration data representative of the vibration of the blade 834*a*. As described elsewhere herein, vibration sensor 844*a* can be positioned on the blade 834*a* itself, on a blade holder supporting the blade 834*a*, or the like. In some embodiments, blade 834*a* includes a plurality of vibration sensors for measuring the vibration of various portions of the blade (e.g., one on each end of the blade).

In the example of FIG. 8, the system 800 includes a chemical source 836*a* associated with roller 832*a*. Chemical source 836*a* can be configured to apply one or more chemicals to the roller 832*a* and/or blade 834*a*. In some examples, chemical source 836*a* can selectively provide one or more of a plurality of chemicals to the roller 832*a* and/or blade 834*a*. Exemplary chemicals can include, but are not limited to, water, dispersants, surfactants, coagulants, solvents, detackifiers, fixitives, and the like.

System 800 further includes a controller 850 in communication with the vibration sensor 844*a*. The controller 850 can be configured to receive vibration data from the vibration sensor 844, analyze the vibration data, and determine if one or more predetermined conditions (e.g., excess vibration) is present at the blade 834*a*. The controller 850 may be configured to determine information regarding the status of system 800, or at least of the blade 834*a* and/or roller 832*a*, based on the analyzed vibration data received from vibration sensor 844*a*. Such information may include the buildup of deposits on roller 832*a* and/or conditions that may lead to excessive buildup of such deposits. Additionally or alternatively, such information can include one or more corrective actions that can reduce the amount of deposits, the rate of deposit formation, and/or the likelihood of future deposits.

In some embodiments, the controller 850 is configured to communicate with the chemical source 836*a* to control the application of one or more chemicals from the chemical source 836*a* to the roller 832*a* and/or the blade 834*a*. The controller 850 can determine, based on analysis of received vibration data, one or more corrective actions to address detected one or more detected conditions, such as excess vibration. For example, the controller 850 can cause the chemical source 836*a* to apply a chemical to roller 832*a* and/or blade 834*a* to assist in the removal of deposits such as stickies on the roller 832*a*. In some embodiments, a chemical source can be capable of providing one or more of a plurality of chemicals to a corresponding roller and/or blade to reduce and/or prevent deposits on the roller. In some examples, the controller 850 can selectively cause a chemical source to provide a certain chemical or combination of chemicals based on the analyzed vibration data. For instance, in an exemplary embodiment, the controller 850 may receive vibration data from vibration sensor 844*a* and characterize the vibration data by analyzing the frequency content of the vibration data. In some such examples, the controller 850 can determine, based on the frequency analysis, a type of deposit forming at the roller, and can cause one or more appropriate chemicals to be selectively applied to address the particular type of deposit forming.

For example, detected stickies can be addressed by dispensing or adjusting the flow of chemistries such as dispersants, surfactants, coagulants, solvents, detackifiers, fixitives, release agents, and the like as described elsewhere herein. Additionally or alternatively, other materials, such as pitch, white pitch, waxes, scaling (e.g., inorganic scale), hydrolyzed ASA (alkenyl succinic anhydride) and/or other paper sizing agents, and/or any of a variety of hydrophobic materials, for example, can similarly form deposits within the paper making system. Similarly, different chemicals can be applied as corrective actions to address such variety of deposit materials. For example, acids may be applied in the system (e.g., via one or more chemical sources 836a or 386b) to address deposits of inorganic scale.

The system of FIG. 8 further includes a roller 832b having associated blade 834b configured such that, as the roller 832b rotates, the surface of roller 832b scrapes against the blade 834b, and a vibration sensor 844b configured to generate vibration data representative of the vibration of blade 834b. The system 800 includes chemical source 836b configured to provide one or more chemicals to roller 832b and/or blade 834b.

In some examples, the controller 850 can be configured to receive and analyze vibration data from the vibration sensor 844b separately from the vibration data from vibration sensor 844a. Accordingly, in some embodiments, detecting one or more predetermined conditions can include, for example, detecting excess vibration at a particular location in the system, such as at blade 834b and not blade 834a. In some such examples, controller can differentiate between detected vibration at each of a plurality of blades and only initiate corrective action where required. For instance, if excess vibration is detected at blade 834b and not blade 834a, the controller may cause chemical source 836b to apply or increase the application of a chemical to roller 832b and/or blade 834b to reduce or inhibit deposits on the roller 832b without adjusting the operation of roller 832a, blade 834a, and chemical source 836a.

In general, systems can include any number of rollers, blades, vibration sensors, chemical sources, and the like. In various examples, the controller is programmed to link certain system components together, such as certain blades, rollers, and chemical sources, so that the controller can initiate corrective actions at separate system components individually.

Additionally or alternatively, in some examples, the controller 850 can be in communication with a variety of other components. For example, as described elsewhere herein, the controller 850 can be in communication with one or more chemical source(s) 856, which can be placed anywhere throughout the system, such as proximate various portions of a carrier running through a portion of the system. Such chemical source(s) 856 can be used to apply one or more chemicals, for example, directly to a carrier at one or more locations within the system.

Similarly, as described elsewhere herein, in various embodiments, the controller 850 can be in communication with one or more vacuum(s)/blower(s) 858 throughout the system that can be used, for example, to facilitate transferring of paper material between system components. In various examples, controller 850 can control one or more vacuum(s)/blower(s) 858 in response to detected vibration (e.g., from vibration sensor 844a or 844b) to reduce the rate or likelihood of deposits forming within the system.

As shown, the controller 850 can be in communication with paper stock preparation location 802, and can control aspects of the paper stock input into the system. Thus, in some examples, the controller 850 can determine, based on analysis of the vibration data, that one or more properties of the paper stock is causing detected one or more predetermined conditions (e.g., excess vibration and/or deposits in the system). In such examples, the controller 850 can control one or more properties of the paper stock via communication with paper stock preparation location 802. In various examples, the controller 850 can control one or more properties of the paper stock, including, but not limited to, feed rate, temperature, furnish, composition, pH, water quality, and the like.

In some embodiments, controller 850 may perform an optimization task, for example, by reducing an amount of chemical applied to a corresponding roller (e.g., 832a) and/or blade (e.g., 834a) if one or more of a set of one or more predetermined conditions (e.g., excess vibration) is not detected. In some examples, the controller 850 can continue to reduce the amount of chemical applied while analyzing the vibration data. In the event that vibration data becomes indicative of one or more predetermined conditions (e.g., of excess vibration, deposits forming, and/or a condition likely to cause deposits to form), the controller 850 can increase the supply of the chemical. Similar optimization processes can be performed for a variety of parameters, including paper stock properties at the headbox, chemistry flow rates, chemistry concentrations, and the like. The results of such optimization tasks can be stored in a memory to establish baseline parameters (e.g., chemistry flow rates, paper stock feed rates, etc.) for system operation.

In the example of FIG. 8, the controller 850 is in communication with a user interface 852. In some examples, the controller can receive programming instructions such as updated processing instructions for analyzing vibration data via the user interface 852. Such instructions can include, for example, chemical programs correlating certain detected vibration data to certain chemical responses (e.g., application of chemicals via chemical sources, adjusting the chemistry of a paper stock, etc.). Additionally or alternatively, the controller 850 can output information to the user interface 852 for analysis by a user. For example, in some instances, the controller 850 may determine one or more corrective actions to be performed to address excess detected vibration (e.g., step 778 in FIG. 7), but may be unable to execute the action itself. Thus, initiating the appropriate corrective action can include providing an output to a user via the user interface 852 to signal a user to perform the corrective action. Such corrective actions could include applying a chemical at one or more system locations, replenishing a chemical supply, adjusting the paper stock (e.g., the furnish), shutting down the system, cleaning one or more components, changing a blade, changing the furnish, applying a chemical, checking for a structural malfunction (e.g., of the blade holder), changing the loading pressure, purging the system, or the like.

In the illustrated example of FIG. 8, the system 800 further includes one or more auxiliary sensors 854. Auxiliary sensors 854 can be used to provide additional information to the controller 850 which can be used in analyzing the vibration data. Exemplary auxiliary sensors can include temperature sensors configured to measure temperature of, for example, ambient temperature, paper stock temperature, applied chemical temperature, and the like. Other examples of auxiliary sensors can include pH sensors, concentration sensors, conductivity sensors, turbidity sensors, effluent monitoring sensors (e.g., turbidity and/or pH), optical sensors (e.g., optical stickies monitoring), or other sensors that can provide useful information in a paper making process.

As described elsewhere herein, data from such variety of sensors can provide useful information regarding various aspects of the system as well as possible corrective actions to address certain types of problems. In some examples, one or more predetermined conditions can be based on data from the auxiliary sensor(s) 854 used in conjunction with vibration data from vibration sensors (e.g., 844a, 844b) to determine whether or not the predetermined condition is met and/or to determine an appropriate action for addressing the condition.

In various embodiments, controller 850 can be positioned on-site at the paper making facility, for example, embodied as a computer system running local software for interfacing with the paper making system. In other examples, the controller 850 can be located remotely from the system, for example, in a central processing center, in the cloud, or the like. In some such examples, on-site components such as vibration sensors, chemical sources, the headbox, a user interface, and the like, can be in communication with a network for communicating data to and/or receiving data from the controller.

While often described with respect to adjusting properties of the paper stock provided at the headbox and/or adjusting the supply of one or more chemicals provided to rollers and/or corresponding blades, other system parameters may be similarly adjusted as one or more corrective actions to address one or more detected predetermined conditions (e.g., excess vibration). For example, with reference to FIG. 3, operation of one or more additional chemical sources 338a-e and/or vacuums/blowers 340a-c can be controlled to address such detected condition(s). In various embodiments, different combinations of such components can be operated in response to different detected vibration characteristics. For example, certain chemical sources 338a-e and/or vacuums/blowers 340a-c can be operated in response to vibration detected at a certain blade (e.g., 334a-c).

Additionally, while in the illustrated example of FIG. 3, blades 334a, 334b, 334c are used to clean rollers 332a, 332b, 332c that engage the paper side 314 of carrier 312, similar blades can be disposed proximate any roller in the system, for example, for cleaning such rollers. Similar vibration sensors can be employed to monitor the vibration of such blades similar to the vibration analysis discussed elsewhere herein. Similarly, while often described with respect to components in the carrier conditioning section (e.g., 330 in FIG. 3), such blades need not engage rollers exclusively in the carrier condition section. Rather, blades for which corresponding vibration data is analyzed can similarly be used to engage rollers throughout the system (e.g., roller 311, press roller 318, etc.). In general, vibration data associated with any rollers that may experience deposits such as stickies may be used to characterize deposit conditions in the system and to initiate subsequent actions to address any detected predetermined conditions (e.g., excess vibration).

Various embodiments have been described. Such examples are non-limiting, and do not define or limit the scope of the invention in any way. Rather, these and other examples are within the scope of the following enumerated embodiments.

The invention claimed is:

1. A paper making system comprising:
   a plurality of guide rollers including a first guide roller;
   a carrier forming a continuous surface contacting the plurality of guide rollers, the carrier having a paper side and a back side and being configured to travel in a first direction around the plurality of guide rollers during a paper making process;
   a paper stock source configured to provide a paper stock to the paper side of the carrier;
   a cleaning blade arranged to clean the first guide roller;
   an accelerometer configured to detect vibration of the cleaning blade; and
   a controller in communication with the accelerometer and configured to:
      receive vibration data from the accelerometer;
      analyze the received vibration data to determine a character of the vibration of the cleaning blade as indicated by the vibration data;
      differentiate between a plurality of causes of the vibration of the cleaning blade based on the determined character to determine a cause of the vibration of the cleaning blade; and
      if the vibration data satisfies a predetermined condition, initiate a corrective action based on the cause of the vibration of the cleaning blade.

2. The system of claim 1, wherein:
   analyzing the received vibration data comprises determining an amount of deposit on the first guide roller associated with the cleaning blade; and
   the controller is configured to initiate the corrective action if the determined amount of deposit satisfies a predetermined condition.

3. The system of claim 2, wherein the determined amount of deposit comprises a determined amount of stickies deposited on the first guide roller from the carrier.

4. The system of claim 1, further comprising:
   a second guide roller in the plurality of guide rollers;
   a second cleaning blade arranged to clean the second guide roller; and
   a second accelerometer in communication with the controller and configured to detect vibration of the second cleaning blade;
   wherein the controller is further configured to:
      receive second vibration data from the second accelerometer; and
      analyze the second vibration data from the second accelerometer,
      wherein the initiated corrective action is based on both the analyzed vibration data and the analyzed second vibration data.

5. The system of claim 1, wherein the first guide roller is positioned such that, the carrier travels, in the first direction, (i) from the paper stock source to a first interface where the paper stock is transferred from the carrier to an interfacing component such that the carrier is substantially free of the paper stock as it encounters the first guide roller, (ii) from the first interface to the first guide roller, and (iii) from the first guide roller to the paper stock source.

6. The system of claim 1, wherein the carrier comprises a felt material.

7. The system of claim 1, further comprising a first chemical source in communication with the controller and wherein initiating the corrective action comprises changing an amount of a chemical dispensed from the first chemical source.

8. The system of claim 7, wherein the chemical comprises one or more from the group consisting of:
   water, fixitives, dispersants, surfactants, coagulants, solvents, release agents, and detackifiers.

9. The system of claim 1, wherein initiating the corrective action comprises alerting a user of the detected vibration.

10. The system of claim 1, wherein initiating the corrective action comprises changing the makeup of the paper stock provided by the paper stock source.

11. The system of claim 1, further comprising:
a second cleaning blade associated with and arranged to clean a second guide roller; and
a second accelerometer coupled to and configured to detect vibration of the second cleaning blade; wherein the controller is in communication with the second accelerometer and is configured to:
receive vibration data from the second accelerometer representative of the vibration of the second cleaning blade;
analyze the vibration data received from the second accelerometer; and
if the vibration data from the second accelerometer satisfies a predetermined condition, initiate a second corrective action.

12. The system of claim 1, wherein analyzing the received vibration data comprises analyzing the frequency content of the received vibration data.

13. The system of claim 12, wherein analyzing the frequency content of the received vibration data comprises determining an amount of vibration present in a plurality of frequency bands; and
the initiated corrective action is selected from a plurality of possible corrective actions based on the frequency content of the vibration data.

14. A method for addressing deposits in a paper making system comprising:
receiving vibration data from one or more accelerometers arranged to sense the vibration of a cleaning blade for cleaning a surface of a roller in the paper making system;
analyzing the received vibration data to determine a character of the vibration of the cleaning blade as indicated by the vibration data;
differentiating between a plurality of causes of the vibration of the cleaning blade based on the determined character to determine a cause of the vibration of the cleaning blade; and
if the vibration data satisfies a predetermined condition, initiating a corrective action based on the cause of the vibration of the cleaning blade.

15. The method of claim 14, wherein analyzing the received vibration data comprises analyzing the frequency content of the received vibration data and determining an amount of vibration present in a plurality of frequency bands, and wherein the initiated corrective action is selected from a plurality of possible corrective actions based on the frequency content of the vibration data.

16. The method of claim 14, wherein the roller is in a wet end of the paper making system.

17. The method of claim 14, wherein initiating the corrective action comprises adjusting an amount of at least one chemical provided to the system, and wherein the at least one chemical comprises one selected from the group consisting of:
water, fixatives, dispersants, surfactants, coagulants, solvents, release agents, and detackifiers.

18. A paper making system comprising:
a plurality of rollers engaging a carrier for transporting paper stock through the system;
a cleaning blade positioned proximate a first roller in the plurality of rollers, the cleaning blade being configured to contact a surface of the first roller so that, as the first roller rotates, the surface of the first roller scrapes against the cleaning blade;
an accelerometer positioned relative to the cleaning blade so that the accelerometer detects vibrations of the cleaning blade as the cleaning blade contacts the surface of the first roller; and
a controller in communication with the accelerometer, the controller being configured to:
receive vibration data from the accelerometer;
differentiate between a plurality of causes of the vibration of the cleaning blade based on a character of the vibration of the cleaning blade, as indicated by the vibration data, to determine a cause of the vibration of the cleaning blade; and
if the received vibration data from the accelerometer satisfies a predetermined condition, initiating a corrective action based on the cause of the vibration of the cleaning blade.

19. The paper making system of claim 18, wherein the accelerometer is positioned on the cleaning blade or a cleaning blade holder configured to support the cleaning blade.

20. The paper making system of claim 18, further comprising a second accelerometer positioned on the cleaning blade or the cleaning blade holder such that the first and second accelerometers are positioned proximate opposite ends of the cleaning blade.

21. The paper making system of claim 18, wherein the controller is configured to determine, from the received vibration data, an amount of deposit formed on the first roller.

22. The paper making system of claim 18, wherein the initiating the corrective action comprises:
(i) alerting a user
(ii) adjusting one or more properties of the paper stock; and/or
(iii) adjusting an amount of at least one chemical applied to the system, the at least one chemical being one or more from the group consisting of:
water, fixatives, dispersants, surfactants, coagulants, solvents, release agents, and detackifiers.

23. The paper making system of claim 22, wherein the controller is further configured to analyze the frequency content of the received vibration data by determining an amount of vibration present in a plurality of frequency bands.

24. The paper making system of claim 23, wherein the one or more initiated corrective action is selected based on the frequency content of the vibration data.

* * * * *

UNITED STATES PATENT AND TRADEMARK OFFICE
CERTIFICATE OF CORRECTION

| | | |
|---|---|---|
| PATENT NO. | : 11,041,271 B2 | Page 1 of 1 |
| APPLICATION NO. | : 16/169513 | |
| DATED | : June 22, 2021 | |
| INVENTOR(S) | : Dominic Luneau et al. | |

It is certified that error appears in the above-identified patent and that said Letters Patent is hereby corrected as shown below:

In the Specification

In Column 2, Line 21, delete "fixitives," and insert -- fixatives, --

In Column 5, Line 29, delete "fixitives," and insert -- fixatives, --

In Column 12, Line 27, delete "fixitives," and insert -- fixatives, --

In Column 13, Lines 3-4, delete "fixitives," and insert -- fixatives, --

In the Claims

In Column 16, Claim 8, Line 61, delete "fixitives," and insert -- fixatives, --

In Column 17, Claim 17, Line 56, delete "fixitives," and insert -- fixatives, --

In Column 18, Claim 22, Line 47, delete "fixitives," and insert -- fixatives, --

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*